United States Patent [19]

Mitsuhashi

[11] Patent Number: 4,784,946

[45] Date of Patent: Nov. 15, 1988

[54] METHOD FOR ASSAYING THE GAMMA-INTERFERON PRODUCTIVITY OF BLOOD

[75] Inventor: Masakazu Mitsuhashi, Okayama, Japan

[73] Assignee: Kabushiki Kaisha Hayashibara Seibutsu Kagaku Kenkyujo, Okayama, Japan

[21] Appl. No.: 809,756

[22] Filed: Dec. 17, 1985

[30] Foreign Application Priority Data

Dec. 30, 1984 [JP] Japan ................... 59-280697
Dec. 30, 1984 [JP] Japan ................... 59-280698

[51] Int. Cl.$^4$ ............................................ C12Q 1/02
[52] U.S. Cl. ..................................... 435/29; 435/4; 435/28; 435/811; 436/64
[58] Field of Search ................ 435/29, 241, 7, 68, 435/811; 424/85; 530/351; 436/518, 536, 804

[56] References Cited

U.S. PATENT DOCUMENTS

4,296,025 10/1981 Sugimoto .
4,382,027 5/1983 Braude ............................... 424/85
4,490,357 12/1984 Skurkovich et al. .............. 424/85
4,514,507 4/1985 Secher .

FOREIGN PATENT DOCUMENTS

0063482 10/1982 European Pat. Off. ......... 435/172.3
8404887 12/1984 European Pat. Off. .
4428374 3/1974 Japan .
9400878 9/1978 Japan .
2146027A 4/1985 United Kingdom .

OTHER PUBLICATIONS

H. Strander et al., "Production of Interferon by Human Leukocytes in Vitro," *Ann. Med. exp. Fenn.*, 1966: 265-273.
J. Salk, "A Simplified Procedure for Titrating Hemagglutinating Capacity of Influenza—Virus and the Corresponding Antibody," *The Journal of Immunology*, vol. 49, pp. 87-98, (1944).
A. L. R. Pidot, "Dye Uptake Assay: An Efficient and Sensitive Method for Human Interferon Titration," *Applied Microbiology*, Oct. 1971, pp. 671-677.
Horn et al., "Interferon as Possible Tumor Marker in Breast Cancer," *Proc. Trienn. World Cong. World Cong. World Assoc. Soc. Pathol.* (Anat. Clin.), 1981 (pub. 1982), 1, 277-282.
Flow Laboratories, Inc., "Product Catalog", (1983), pp. 44-45 & 70.
Unanue et al., (1987), Science, vol. 236, pp. 551-557.
O Malley, (1981), Methods of Enzymology, vol. 78, pp. 540-545.
Epstein et al., (1974), Clinical and Experimental Immunology, vol. 16, pp. 553-563.

*Primary Examiner*—Sam Rosen
*Attorney, Agent, or Firm*—Browdy and Neimark

[57] ABSTRACT

Production of HuIFN-gamma and assay of blood HuIFN-gamma productivity both using donated blood are disclosed. Human whole blood secrets a high titer of HuIFN-gamma when exposed to an IFN-gamma inducer (e.g. mitogen) in the presence of anticoagulant (e.g. heparin, ACD, and CPD). Blood HuIFN-gamma productivity is determined by titrating the secreted HuIFN-gamma with a suitable procedure (e.g. bioassay, radio-immunoassay, or enzyme-linked immunosorbent assay). The blood of cancer patient is lower in HuIFN-gamma productivity than that of healthy donor. The HuIFN-gamma per se is recovered and purified prior to its prophylactic and therapeutic uses.

18 Claims, No Drawings

METHOD FOR ASSAYING THE GAMMA-INTERFERON PRODUCTIVITY OF BLOOD

FIELD OF THE INVENTION

The present invention relates to a process for producing humanspecific gamma-interferon (abbreviated as "HuIFN-gamma" hereinafter) using human whole blood and to a method for assaying the HuIFN-gamma productivity of human blood.

DESCRIPTION OF THE PRIOR ART

In recent years, clinical tests whereby the level of serum enzyme or its metabolite is determined chemically have been in wide use.

Since HuIFN-gamma, a blood component, exhibits antiviral- and antitumor-activities, it has been suggested to include the measurement of serum HuIFN-gamma level in clinical test. Such suggestion, however, has not been realized because serum HuIFN-gamma exists in minute amounts.

Blood comprises a fluid, plasma, in which formed elements such as erythrocyte, leukocyte and platelet are suspended. One $mm^3$ of blood from an adult generally contains, in addition to $7.4 \times 10^3$ leukocytes and $3 \times 10^5$ platelets, $5.4 \times 10^6$ erythrocytes in man or $4.8 \times 10^6$ in woman.

It is well known that HuIFN-gamma is produced by human leukocyte.

In conventional processes to produce HuIFN-gamma, viable leukocytes separated from human blood are used. As is evident from, for example, Y.K. Yip et al., *Infection and Immunity*, Vol. 34, pp. 131–139 (1981), and T. Kasahara et al., *The Journal of Immunology*, Vol. 130, No. 4, pp. 1784–1789 (1983), leukocytes are separated from other elements present in whole blood, and then allowed to secrete HuIFN-gamma.

Detailed studies on these conventional processes confirmed that these processes, however, give a low recovery yield of leukocytes from blood, i.e. 30–50%, of the leukocytes are damaged during the separation to lower the viability to 40–60%, and, eventually, lower the overrall recovery yield to approximately 10–30%, as well as that the separated leukocytes give an inconsistent HuIFN-gamma production. These render the determination of blood HuIFN-gamma productivity very difficult, and cause one obstacle in mass-production of HuIFN-gamma.

DETAILED DESCRIPTION OF THE INVENTION

As the results of researches for the mass-production of HuIFN-gamma using precious human blood, as well as for the assay of blood HuIFN-gamma productivity using donated blood, the present inventor found that a large amount of HuIFN-gamma can be easily produced by incubating whole blood in a vessel while exposing the whole blood to an anticoagulant and a gamma-interferon inducer (IFN-gamma inducer). The present inventor also found that blood HuIFN-gamma productivity can be determined with ease and high reproducibility by incubating whole blood in a vessel while exposing the whole blood to an anticoagulant and an IFN-gamma inducer, and titrating the accumulated HuIFN-gamma.

Detailed studies confirmed that the exposure to an IFN-gamma inducer in an amount of 10–10,000 micrograms/ml whole blood is favorable.

The wording of "whole blood" means fresh blood preparations collected from donors, and also suspensions which are obtained by removing the plasma liquid from fresh blood preparations and suspending the residual formed elements in a suitable non-plasma liquid, e.g. saline, buffer solution or nutrient culture medium.

The anticoagulants usable in the invention are those which prevent the coagulation of whole blood, and which do not affect HuIFN-gamma production thereof. Examples of such anticoagulants are heparin, acid citrate-dextrose (ACD), and citrate-phosphate-dextrose (CPD).

The IFN-gamma inducer usable in the invention are those which induce HuIFN-gamma production in whole blood. Examples of such IFN-gamma inducers are mitogens such as phytohaemagglutinin; concanavalin A; pokeweed mitogen; staphylococcal enterotoxin (SEA); lipopolysaccharide; endotoxin; polysaccharide including $\beta$-glucan and arabinogalactan; and bacteria including those of genera Pseudomonas and Corynebacterium.

Specifically, we found that phytohaemagglutinin induces a high HuIFN-gamma titer generally within a relatively brief time of 10–30 hours.

The appropriate range for IFN-gamma inducer inoculum is 10–10,000 micrograms/ml whole blood.

One or more alpha-interferon inducers (HuIFN-alpha inducers), such as virus and nucleic acid, can be used together with HuIFN-gamma inducer to enhance HuIFN-gamma production and/or to induce simultaneous HuIFN-alpha production.

The step of incubating whole blood in a vessel in the presence of anticoagulant and IFN-gamma inducer is carried out in such a manner that the whole blood contacts with the anticoagulant and IFN-gamma inducer in the vessel to secrete HuIFN-gamma. For example, to the prescribed amounts of anticoagulant and IFN-gamma inducer in a vessel is added an appropriate amount of whole blood, and the mixture is incubated in the vessel. Alternatively, a mixture of anticoagulant and whole blood is placed in a vessel, added with an IFN-gamma inducer, and incubated in the vessel. In this incubation step, a suitable medium, e.g. saline, isotonic buffer or nutrient culture medium, may be added.

Tank, jar, flask, test tube, ampul and micro plate well of any shape and capacity can be used as the vessel.

The incubation conditions are those under which HuIFN-gamma is producible: for example, temperature range of 30°–40° C.; and 10–90 hours of incubation. Priming and/or superinduction can be carried out during HuIFN-gamma production, if necessary.

The whole blood which has been incubated to produce HuIFN-gamma is then optionally diluted with saline or isotonic buffer, and separated with suitable procedure(s), such as centriguation or filtration, to remove the formed elements such as blood cells. Thereafter, the resultant supernatant or filtrate containing HuIFN-gamma is subjected to purification or HuIFN-gamma titration.

The HuIFN-gamma can be easily purified by combination of conventional procedures, e.g. salting-out, dialysis, filtration, concentration, adsorption and desorption by ion exchange, gel filtration, affinity chromatography using a suitable ligand such as antibody, isoelectric point fractionation and electrophoresis, to obtain a high-purity HuIFN-gamma.

The HuIFN-gamma thus obtained is advantageously usable in injection or drug for external or internal use in the prevention and treatment of human diseases. It may be used alone or in combination with one or more substances, e.g. antiviral agent, immunoactivator, antioncotic, etc.

Any assay method is employable in the invention as long as the HuIFN-gamma produced by whole blood is titrated thereby. Specifically suited are the bioassay, radioimmunoassay and enzyme-linked immunosorbent assay.

In recent years, the enzyme-linked immunosorbent assay has been developed as a highly safe, convenient and speedy assay. Any enzymelinked immunosorbent assay is employable as long as HuIFN-gamma is titrated as the antigen thereby. Examples of such enzyme-linked immunosorbent assays are the double antibody sandwich technique and modified double antibody sandwich technique.

It was confirmed that the HuIFN-gamma productivity determined in this way is useful for testing the individual donor clinically.

The method according to the invention confirmed that the blood collected from a cancer patient is much lower in HuIFN-gamma productivity than those collected from healthy donors.

The following experiments further explain the present invention.

EXPERIMENT 1

Effect of pretreatment on blood HuIFN-gamma productivity

The effect of pretreatment on blood HuIFN-gamma productivity was studied. In this Experiment, fresh blood specimens collected from three healthy donors were used after heparinization.

The treated bloods used in this Experiment were as follows: a plasma-free suspension, obtained by centrifuging blood to remove the plasma liquid and suspending the residual formed elements in RPMI 1640 medium to give the same element density as that in blood; and an ammonium chloride-treated suspension, obtained by treating blood with Tris-HCl buffer (pH 7.2) containing 0.75% ammonium chloride in usual way to effect the haemolysis of the erythrocytes, centrifuging the mixture and suspending the resultant erythrocyte-free formed elements in RPMI 1640 medium to give the same element density as that in blood.

One ml aliquots of either heparinized or treated blood were placed in plastic test tubes which were then added with 0.1 ml aliquots of saline containing phytohaemagglutinin-P in respective amount of 0, 50 or 500 micrograms, followed by 24-hour incubation at 37° C. The supernatants obtained by centrifuging the incubated mixtures were assayed for HuIFN-gamma titers per ml whole blood.

The HuIFN-gamma titers were determined with the use of "GAMMA INTERFERON IRMA KIT", a radioimmunoassay kit for HuIFN-gamma, commercialized by Celltech, Ltd., Berkshire, England.

The results are given in Table 1.

These evidences clearly confirm that whole blood and plasmafree suspension containing the whole formed elements of blood are suitable for specimen for determining blood HuIFN-gamma productivity because they give a high and consistent HuIFN-gamma titer. Also was confirmed that the ammonium chloride-treated suspension wherein the erythrocytes were haemolyzed and removed gives a low and inconsistent HuIFN-gamma titer.

TABLE 1

| Treatment | Phytohaemagglutinin (microgram) | Healthy donor | | |
|---|---|---|---|---|
| | | A | B | C |
| No treatment | 0 | 0 | 0 | 0 |
| | 50 | 230 | 200 | 280 |
| | 500 | 540 | 600 | 620 |
| Plasma-free suspension | 0 | 0 | 10 | 0 |
| | 50 | 220 | 230 | 240 |
| | 500 | 570 | 640 | 670 |
| Ammonium chloride-treated suspension | 0 | 0 | 10 | 0 |
| | 50 | 0 | 30 | 20 |
| | 500 | 0 | 40 | 10 |

EXPERIMENT 2

Effect of IFN-gamma inducer inoculum on blood HuIFN-gamma productivity

The effect of IFN-gamma inducer inoculum on blood HuIFN-gamma productivity was studied. Fresh blood specimens collected from three healthy donors and two cancer patients, i.e. liver cancer patient and stomach cancer patient, were used after heparinization.

According to the method in Experiment 1, one ml aliquots of either heparinized blood specimen were placed in test tubes, added with 0.1 ml aliquots of saline containing phytohaemagglutinin-P as the IFN-gamma inducer in respective amount of 0, 1, 10, 10, 1,000 or 10,000 micrograms, incubated and assayed for HuIFN-gamma titers per ml blood.

A series of experiments using 100,000 micrograms of phytohaemagglutinin-) per ml blood was planed, but omitted because dissolution of such amount of phytohaemagglutinin was unsuccessful.

The results are given in Table 2.

TABLE 2

| Phytohaemagglutinin (microgram) | Healthy donor | | | Cancer patient | |
|---|---|---|---|---|---|
| | D | E | F | G | H |
| 0 | 0 | 0 | 0 | 0 | 0 |
| 1 | 0 | 0 | 0 | 0 | 0 |
| 10 | 130 | 100 | 120 | 0 | 0 |
| 100 | 410 | 380 | 430 | 0 | 10 |
| 1,000 | 680 | 620 | 760 | 0 | 20 |
| 10,000 | 670 | 660 | 710 | 0 | 20 |
| 100,000 | ND | ND | ND | ND | ND |

Note: ND means not done; patient G, liver carcinoma patient; and patient H, stomach cancer patient.

These evidences clearly confirmed that IFN-gamma inducer inocula of 10–10,000 micrograms/ml blood are favorable.

Also was confirmed that the blood collected from a cancer patient is much lower in HuIFN-gamma productivity than those collected from healthy donors. After determining the HuIFN-gamma productivites of whole blood specimens collected from twenty healthy donors and twenty cancer patients using 100 micrograms of IFN-gamma inducer per ml whole blood, it was found that the HuIFN-gamma productivity of healthy donor was 420±100 units/ml blood, while that of cancer patient was 10±10 units/ml blood. This suggests that the assay of donated blood on its HuIFN-gamma productivity would be helpful for the detection of cancer in its early stage.

Several embodiments of the present invention will be disclosed.

EXAMPLE A

Assay of blood HuIFN-gamma productivity

Example A-1

One ml heparinized specimen of a fresh blood from a 28 years old healthy man was placed in a plastic test tube, added with 250 micrograms of phytohaemagglutinin-P, and incubated at 37° C., for 24 hours. The supernatant obtained by centrifuging the incubated mixture was assayed for HuIFN-gamma titer with the radioimmunoassay kit similarly as in Experiment 1.

The HuIFN-gamma productivity was about 420 units/ml blood.

EXAMPLE A-2

One ml heparinized specimen of a fresh blood from a 33 year old healthy woman was added with 500 micrograms of concanavalin A, and incubated at 37° C. for 64 hours. The incubated mixture was then assayed for HuIFN-gamma titer similarly as in Example A-1.

The HuIFN-gamma productivity was about 380 units/ml blood.

EXAMPLE A-3

A heparinized specimen of a fresh blood from a 61 years old healthy man was centrifuged to remove the plasma. The formed elements so obtained were then centrifugally washed in saline, and suspended in RPMI 1640 medium to give the same element density as that in blood.

One ml of the resultant suspension was placed in a plastic test tube, added with 300 micrograms of poke-weed mitogen, and incubated at 37° C. for 48 hours. Thereafter, the HuIFN-gamma titer of the resultant specimen was assayed with the double antibody sandwich technique, an enzyme-linked immunosorbent assay.

The HuIFN-gamma productivity was about 200 units/ml blood. The value determined with the enzyme-linked immunosorbent assay was in good consistency with the radioimmunoassay value.

EXAMPLE A-4

A heparinized specimen of a fresh blood from a 58 years old male lung cancer patient was treated similarly as in Example A-1 to obtain an HuIFN-gamma productivity of about 20 units/ml blood.

EXAMPLE A-5

A heparinized specimen of a fresh blood from a 55 years old female hysterocarcinoma patient was treated similarly as in Example A-1 to obtain an HuIFN-gamma productivity of about 10 units/ml blood.

EXAMPLE B

Production of HuIFN-gamma

EXAMPLE B-1

One ml heparinized specimen of a fresh blood from a healthy volunteer was placed in a plastic test tube, added with 250 micrograms of phytohaemagglutinin-P, and incubated at 37° C. for 24 hours. The supernatant obtained by centrifuging the incubated mixture was assayed for HuIFN-gamma titer.

The HuIFN-gamma production was about 420 units/ml blood.

EXAMPLE B-2

One ml heparinized specimen of a fresh blood from a healthy donor was added with 500 micrograms of concanavalin A, incubated at 37° C. for 64 hours, and assayed for HuIFN-gamma titer. The HuIFN-gamma production was about 380 units/ml blood.

EXAMPLE B-3

A heparinized specimen of a fresh blood from healthy donors was centrifuged to remove the blood plasma, and the residual formed elements were centrifugally washed in saline. The formed elements were then suspended in RPMI 1640 medium to give the same element density in blood.

The suspension was then placed in a mini jar, added with poke-weed mitogen in an amount of 200 micrograms/ml suspension, incubated at 37° C. for 64 hours, and assayed for HuIFN-gamma titer similarly as in Example B-1.

The HuIFN-gamma production was about 240 units/ml blood.

EXAMPLE B-4

A suspension of blood formed elements was prepared similarly as in Example B-3.

The suspension was placed in a mini jar, added with phytohaemagglutinin-P in an amount of 500 micrograms/ml suspension, incubated at 37° C. for 28 hours, and assayed for HuIFN-gamma titer similarly as in Example B-1.

The HuIFN-gamma production was about 600 units/ml blood.

It will be obvious to those skilled in the art that various changes and alterations may be made without departing from the scope of the invention and the invention is not to be considered limited to what is described in the specification.

I claim:

1. A clinical assay for detecting human cancer, said method comprising the steps of:
    (a) collecting fresh human whole blood from a patient suspected of having cancer;
    (b) incubating said human whole blood at a temperature in the range of 30–40° C. for 10–90 hours while exposing it to an anticoagulant and a gamma-interferon inducer (IFN-gamma inducer); and
    (c) determining the level of HuIFN-gamma in the resultant culture
    (d) comparing said level of HuIFN-gamma against a standard determined by measuring the HuIFN-gamma productivity of whole blood collected from a healthy patient and incubated under the conditions of step (b)
    (e) whereby an HuIFN-gamma level obtained by said culturing of said blood of said suspected cancer patient which is significantly lower than said standard indicates the presence of cancer.

2. The method in accordance with claim 1, wherein the amount of said IFN-gamma inducer is in the range of 10–10,000 micrograms/ml whole blood or said suspension.

3. The method in accordance with claim 1, wherein said anti-coagulant is selected from the group consisting of heparin, acid citrate-dextrose, citrate-phosphate-dextrose and mixtures thereof.

4. The method in accordance with claim 1, wherein said IFN-gamma inducer is a mitogen.

5. The method in accordance with claim 1, wherein said IFN-gamma inducer is a member selected from the group consisting of phytohaemagglutinin, concanavalin A, pokeweed mitogen, staphylococcal enterotoxin, lipopolysaccharide, endotoxin, polysaccharide, bacterium, and mixtures thereof.

6. The assay of claim 1, wherein the determining step is effected by bioassay.

7. The assay of claim 1, wherein the determining step is effected by radioimmunoassay.

8. The assay of claim 1 wherein the determining step is effected by enzyme-linked immunosorbent assay.

9. The assay of claim 1, consisting essentially of said collecting, incubating, determining and comparing steps.

10. The assay of claim 4, wherein the amount of the interferon-gamma inducer is in the range of 10–10,000 micrograms/ml whole blood.

11. A clinical assay for detecting human cancer, comprising:
 (a) collecting whole blood from a subject;
 (b) removing the plasma from the donated whole blood;
 (c) suspending the residual solid in a member selected from the group consisting of saline, isotonic buffer, and a nutrient culture medium;
 (d) incubating in vitro a predetermined amount of the resultant cell suspension at temperature in the range of 30°–40° C. for 10–90 hours while exposing it to an anticoagulant and an interferon-gamma inducer; and
 (f) determining the interferon-gamma level in the resultant culture,
 (g) comparing said interferon-gamma level against a standard predetermined by measuring normal level of interferon-gamma obtained by collecting whole blood from a healthy patient and performing steps (b) through (f) upon the collected whole blood;
 (h) whereby a level of interferon gamma obtained by said processing of said blood of said suspected cancer patient according to steps (b) through (f) significantly below said standard indicates the presence of cancer.

12. The assay of claim 11, wherein said anticoagulant is a member selected from the group consisting of heparin, acidcitrate-dextrose, citrate-phosphate-dextrose, and mixtures thereof.

13. The assay of claim 11, wherein said interferon gamma inducer is a mitogen.

14. The assay of claim 11, wherein said interferon gamma inducer is a member selected from the group consisting of phytohaemagglutinin, concanavalin A pokeweed mitogen, staphylococcal enterotoxin, lipopolysaccharide, endotoxin, polysaccharide, bacterium, and mixtures thereof.

15. The assay of claim 11, wherein the determining step is effected by bioassay.

16. The assay of claim 11, wherein the determining step is effected by radioimmunoassay.

17. The assay of claim 11, wherein the determining step is effected by enzyme-linked immunosorbent assay.

18. The assay of claim 11, consisting essentially of said collecting, removing, suspending, incubating, determining and comparing steps.

* * * * *